United States Patent [19]
Platz et al.

[11] Patent Number: 5,284,656
[45] Date of Patent: Feb. 8, 1994

[54] PULMONARY ADMINISTRATION OF GRANULOCYTE COLONY STIMULATING FACTOR

[75] Inventors: Robert M. Platz, Half Moon Bay; Mark A. Winters, Mountain View; Colin G. Pitt, Thousand Oaks, all of Calif.

[73] Assignee: Amgen Inc., Thousand Oaks, Calif.

[21] Appl. No.: 953,208

[22] Filed: Sep. 29, 1992

Related U.S. Application Data

[63] Continuation of Ser. No. 669,792, Mar. 15, 1991, abandoned.

[51] Int. Cl.$^5$ .................. A61K 9/14; A61K 45/05; C07K 17/10; C07K 15/14
[52] U.S. Cl. ........................... 424/435; 424/43; 424/46; 424/85.1; 424/434; 514/2; 514/8; 514/21; 514/885; 514/951; 530/350; 530/395; 530/397; 530/838
[58] Field of Search ................. 424/43, 46, 85.1, 434, 424/435; 514/2, 8, 21, 885; 530/951, 350, 395, 397, 838

[56] References Cited

U.S. PATENT DOCUMENTS

| | | | |
|---|---|---|---|
| 4,833,127 | 5/1989 | Ono et al. | 514/21 |
| 4,961,926 | 10/1990 | Gabrilove | 514/2 |
| 5,043,156 | 9/1991 | Matsumoto et al. | 514/8 |

Primary Examiner—Thurman K. Page
Assistant Examiner—Carlos Azpuru
Attorney, Agent, or Firm—Richard J. Mazza

[57] ABSTRACT

Granulocyte-colony stimulating factor (G-CSF) can be delivered systemically in therapeutically or prophylactically effective amounts by pulmonary administration using a variety of pulmonary delivery devices, including nebulizers, metered dose inhalers and powder inhalers. Aerosol administration in accordance with this invention results in significant elevation of the neutrophil levels that compares favorably with delivery by subcutaneous injection. G-CSF can be administered in this manner to medically treat neutropenia, as well as to combat or prevent infections.

21 Claims, 3 Drawing Sheets

PULMONARY ADMINISTRATION OF GRANULOCYTE COLONY STIMULATING FACTOR

This is a continuation of copending application Ser. No. 07/669,792 filed on Mar. 15, 1991 now abandoned.

FIELD OF THE INVENTION

The present invention relates to the pulmonary administration of a therapeutic protein and, more particularly, to the systemic administration of therapeutically effective amounts of granulocyte colony stimulating factor (G-CSF) via the respiratory system.

BACKGROUND OF THE INVENTION

G-CSF is a hormone-like glycoprotein which regulates hematopoiesis and is required for the clonal growth and maturation of normal hematopoietic precursor cells found in the bone marrow; Welte et al., Proc. Natl. Acad. Sci., Vol. 82, pp. 1526-1530 (1985). More specifically, G-CSF, when present in low concentrations, is known to stimulate the production of neutrophil granulocytic colonies when used in vitro G-CSF is also known to enhance neutrophil migration; Gabrilove, J., Seminars in Hematology, Vol. 26, No. 2, pp. 1-4 (1989). Moreover, G-CSF can significantly increase the ability of neutrophils to kill tumor cells in vitro through antibody mediated cellular cytotoxicity; Souza et al., Science, Vol. 232, pp. 61-65 (1986).

In humans, endogenous G-CSF is detectable in blood plasma; Jones et al., Bailliere's Clinical Hematology, Vol. 2, No. 1, pp.83-111. G-CSF is produced by fibroblasts, macrophages, T cells, trophoblasts, endothelial cells and epithelial cells and is the expression product of a single copy gene comprised of four exons and five introns located on chromosome seventeen. Transcription of this locus produces a mRNA species which is differentially processed, resulting in the expression of two forms of G-CSF, one version having a mature length of 177 amino acids, the other having a mature length of 174 amino acids. The form comprised of 174 amino acids has been found to have the greatest specific in vivo biological activity. G-CSF is species cross-reactive, such that when human G-CSF is administered to another mammal such as a mouse, canine or monkey, sustained neutrophil leukocytosis is elicited; Moore et al., Proc. Natl. Acad. Sci., Vol. 84, pp. 7134-7138 (1987).

Human G-CSF can be obtained and purified from a number of sources. Natural human G-CSF (nhG-CSF) can be isolated from the supernatants of cultured human tumor cell lines. The development of recombinant DNA technology, see, for instance, U.S. Pat. No. 4,810,643 (Souza), incorporated herein by reference, has enabled the production of commercial scale quantities of G-CSF in glycosylated form as a product of eukaryotic host cell expression, and of G-CSF in nonglycosylated form as a product of prokaryotic host cell expression.

G-CSF has been found to be useful in the treatment of cancer, as a means of stimulating neutrophil production to compensate for hematopoietic deficits resulting from chemotherapy or radiation therapy. The effective use of G-CSF as a therapeutic agent requires that patients be administered systemic doses of the protein. Currently, parenteral administration via intravenous, intramuscular or subcutaneous injection is the preferred route of administration to humans and has heretofore appeared to be the only practical way to deliver therapeutically significant amounts of G-CSF to the bloodstream, although attempts have been made at oral delivery; see, for example, Takada et al., Chem. Pharm. Bull., Vol. 37, No. 3, pp. 838-839 (1989).

The pulmonary delivery of relatively large molecules is not unknown, although there are only a few examples which have been quantitatively substantiated. Leuprolide acetate is a nonapeptide with luteinizing hormone releasing hormone (LHRH) agonist activity having low oral availability. Studies with animals indicate that inhalation of an aerosol formulation of leuprolide acetate results in meaningful levels in the blood; Adjei et al., Pharmaceutical Research, Vol. 7, No. 6, pp. 565-569 (1990); Adjei et al., International Journal of Pharmaceutics, Vol. 63, pp. 135-144 (1990).

Endothelin-1 (ET-1), a 21 amino acid vasoconstrictor peptide produced by endothelial cells, has been found to decrease arterial blood pressure when administered by aerosol to guinea pigs; Braquet et al., Journal of Cardiovascular Pharmacology, Vol. 13, suppl. 5, s. 143-146 (1989).

The feasibility of delivering human plasma $\alpha$1-antitrypsin to the pulmonary system using aerosol administration, with some of the drug gaining access to the systemic circulation, is reported by Hubbard et al., Annals of Internal Medicine, Vol. III, No. 3, pp. 206-212(1989).

Pulmonary administration of alpha-1-proteinase inhibitor to dogs and sheep has been found to result in passage of some of that substance into the bloodstream; Smith et al., J. Clin. Invest., Vol. 84, pp. 1145-1146 (1989).

Experiments with test animals have shown that recombinant human growth hormone, when delivered by aerosol, is rapidly absorbed from the lung and produces faster growth comparable to that seen with subcutaneous injection; Oswein et al., "Aerosolization of Proteins", Proceedings of Symposium on Respiratory Drug Delivery II, Keystone, Colo., March, 1990. Recombinant versions of the cytokines gamma interferon (IFN-$\gamma$) and tumor necrosis factor alpha (TNF-$\alpha$) have also been observed in the bloodstream after aerosol administration to the lung; Debs et al., The Journal of Immunology, Vol. 140, pp. 3482-3488 (1988).

SUMMARY OF THE INVENTION

The present invention is based on the discovery that G-CSF can be administered systemically to a mammal via the pulmonary route. Typically, this is accomplished by directing a stream of a therapeutically effective amount of G-CSF into the oral cavity of the inhaling mammal. Importantly, and surprisingly, substantial amounts of G-CSF are thereby deposited in the lung and absorbed from the lung into the bloodstream, resulting in elevated blood neutrophil levels. Moreover, this is accomplished without the necessity to resort to special measures such as the use of absorption enhancing agents or protein derivatives specifically designed to improve absorption. Pulmonary administration of G-CSF thus provides an effective non-invasive alternative to the systemic delivery of G-CSF by injection.

This invention can be practiced using any purified isolated polypeptide having part or all of the primary structural conformation (i.e., continuous sequence of amino acid residues) and one or more of the biological properties of naturally occurring G-CSF. A number of publications describe methods of producing G-CSFs, including the above mentioned Souza patent and the Welte et al. and Nicola et al. articles.

In general, G-CSF useful in the practice of this invention may be a native form isolated pure from mammalian organisms or, alternatively, a product of chemical synthetic procedures or of procaryotic or eucaryotic host expression of exogenous DNA sequences obtained by genomic or cDNA cloning or by gene synthesis. Suitable procaryotic hosts include various bacterial (e.g., *E. coli*) cells. Suitable eucaryotic hosts include yeast (e.g., *S. cerevisiae*) and mammalian (e.g., Chinese hamster ovary, monkey) cells. Depending upon the host employed, the G-CSF expression product may be glycosylated with mammalian or other eucaryotic carbohydrates, or it may be non-glycocylated. The G-CSF expression product may also include an initial methionine amino acid residue (at position $-1$). The present invention contemplates the use of any and all such forms of G-CSF, although recombinant G-CSF, especially *E. coli* derived, is preferred for reasons of greatest commercial practicality.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of G-CSF. Typically, each formulation is specific to the type of device employed and may involve the use of an appropriate propellant material, in addition to the usual diluents, adjuvants and/or carriers useful in G-CSF therapy. G-CSF formulations which can be utilized in the most common types of pulmonary dispensing devices to practice this invention are now described.

Nebulizer G-CSF Formulation

G-CSF formulations suitable for use with a nebulizer, either jet or ultrasonic, will typically comprise G-CSF dissolved in water at a concentration of about 0.1 to 25 mg of G-CSF per mL of solution. The formulation may also include a buffer and a simple sugar (e.g., for protein stabilization and regulation of osmotic pressure). Examples of buffers which may be used are sodium acetate, citrate and glycine. Preferably, the buffer will have a composition and molarity suitable to adjust the solution to a pH in the range of 3 to 4. Generally, buffer molarities of from 2 mM to 50 mM are suitable for this purpose. Examples of sugars which can be utilized are mannitol and sorbitol, usually in amounts ranging from 1% to 10% by weight of the formulation.

The nebulizer formulation may also contain a surfactant, to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001 and 4% by weight of the formulation. An especially preferred surfactant for purposes of this invention is polyoxyethylene sorbitan monooleate.

Metered Dose Inhaler G-CSF Formulation

G-CSF formulations for use with a metered-dose inhaler device will generally comprise a finely divided powder containing G-CSF suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Powder Inhaler G-CSF Formulation

G-CSF formulations for dispensing from a powder inhaler device will comprise a finely divided dry powder containing G-CSF and may also include a bulking agent, such as lactose, sorbitol, sucrose, or mannitol in amounts which facilitate dispersal of the powder from the device, e.g., 50 to 90% by weight of the formulation. The G-CSF should most advantageously be prepared in particulate form with an average particle size of less than 10 μm (or microns), most preferably 1 to 5 μm, for most effective delivery to the distal lung.

The invention contemplates the administration of therapeutic amounts of the protein, i.e., sufficient to achieve elevation of the neutrophil level in the systemic blood. What constitutes a therapeutically effective amount in a particular case will depend on a variety of factors which the knowledgeable practitioner will take into account, including the normal blood neutrophil level for that subject, the severity of the condition or illness being treated, the degree of neutropenia, the physical condition of the subject, and so forth. In general, a dosage regimen will be followed such that the normal blood neutrophil level for the individual undergoing treatment is restored, at least in cases of abnormally low or depressed blood neutrophil counts. For humans, the normal blood neutrophil level is about 5000 to 6000 neutrophils per microliter of blood. Neutrophil counts below 1000 in humans are generally regarded as indicative of severe neutropenia and as placing the subject at great risk to infection. Clinical studies with cancer patients suffering from chemotherapy-induced neutropenia have shown that subcutaneous injected doses of 3–5 μg/kg every twenty-four hours are effective in elevating acutely deficient blood neutrophil levels above 1000. Based on preliminary results with animals, described below, it is anticipated that for most mammals, including humans, the administered dose for pulmonary delivery (referred to here as the inhalation dose) will be about 3 to 10 times the corresponding subcutaneous dose necessary to achieve a particular blood neutrophil level.

As those skilled in the art will recognize, the operating conditions for delivery of a suitable inhalation dose will vary according to the type of mechanical device employed. For some aerosol delivery systems, such as nebulizers, the frequency of administration and operating period will be dictated chiefly by the amount of G-CSF per unit volume in the aerosol. In general, higher concentrations of protein in the nebulizer solution and, correspondingly, the aerosol will require shorter operating periods. Some devices such as metered dose inhalers may produce higher aerosol concentrations than others and thus will be operated for shorter periods to give the desired result.

Other devices such as powder inhalers are designed to be used until a given charge of active material is exhausted from the device. The charge loaded into the device will be formulated accordingly to contain the proper inhalation dose amount of G-CSF for delivery in a single administration.

While G-CSF has been found useful in treating neutrophil-deficient conditions such as chemotherapy related neutropenia, G-CSF is expected to also be effective in combatting infections and in treating other conditions or illnesses where blood neutrophil levels elevated above the norm can result in medical benefit. As further studies are conducted, information will emerge regarding appropriate dosage levels for the administration of G-CSF in these latter cases. It is expected that the present invention will be applicable as a non-invasive alternative in most instances where G-CSF is administered therapeutically by injection.

DETAILED DESCRIPTION

As mentioned, parenteral administration of G-CSF is known to cause an increase in the number of neutrophils in the peripheral blood. Studies were performed to demonstrate that inhalation of an aerosol of recombinant human G-CSF (rhG-CSF) also causes an increase in the number of blood neutrophils. The rhG-CSF employed was an *E. coli* derived recombinant expression product having the amino acid sequence shown in FIG. 7 of the aforementioned Souza patent comprising the entire hG-CSF polypeptide with an amino terminal methionine group. It can be made by use of the same procedure described therein.

Subcutaneous Administration to Hamsters

Figure 1:
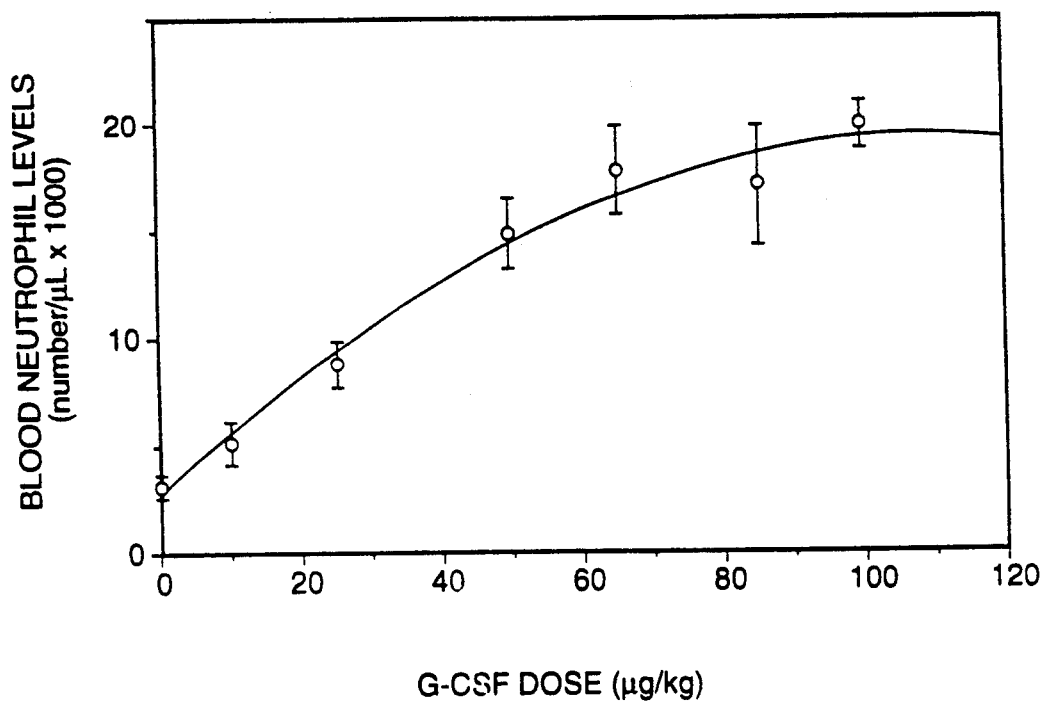
FIG. 1 is a graphical depiction of the effect of subcutaneously administered rhG-CSF on blood neutrophil levels in hamsters.

Initial experiments were performed to measure the change in the number of neutrophils in the blood of 4-6 week old male Golden Syrian hamsters (Charles River Laboratories, Wilmington, Mass.), following subcutaneous administration of various doses of rhG-CSF. The rhG-CSF was prepared as a 4 mg/ml solution in sterile distilled water, diluted in sterile 0.9% saline solution, and different volumes were immediately injected subcutaneously in the lower back of hamsters in test groups of 3 to 5 animals. Twenty-four hours later, blood was collected from each hamster by cardiac puncture under halothane anesthesia. The number of neutrophils in the blood was determined by performing differential and complete blood cell counts. Results of these experiments, shown in FIG. 1, indicate a dose-dependent increase in the number of neutrophils twenty-four hours after injection of rhG-CSF is observed for doses up to approximately 100 micrograms per kilogram of body weight ($\mu$g/kg). The dose response curve appeared to level off at greater doses.

Aerosol Characterization and Administration

Inhalation exposures to aerosols containing rhG-CSF were conducted using a small animal exposure chamber manufactured by In-Tox Products (Albuquerque, N. Mex.). Only the central 12 ports in the animal chamber were used; the peripheral ports in the aerosol distribution manifold in the animal chamber were sealed. With this modification to the chamber, the air supplied by a nebulizer was adequate to maintain 10 hamsters during an exposure. Filter samples were taken from one of the animal ports and from the air exhaust line to measure the aerosol concentration in the exposure chamber. The aerosol was sampled from the remaining available animal port, and particle size distribution measurements with a QCM (quartz crystal monitor) cascade impactor (California Instruments, Inc., Sierra Madre, Calif.) were taken periodically throughout an exposure. This cascade impactor draws only 240 mL/min, which allows the particle size distribution of the aerosol to be measured without disturbing the airflow pattern in the exposure chamber.

Prior to conducting the animal exposure studies, the aerosol concentration and particle size distribution of aerosols generated from a 20 mg/mL albumin solution, using either the Ultravent nebulizer or the Acorn II nebulizer (both jet type), were measured in the exposure chamber. Table 1 shows the particle size distribution and the average albumin concentration in the aerosol measured at two locations(nose and outlet) in the chamber. The Ultravent produced an aerosol having much smaller particles than the Acorn II, but the Acorn II produced a more concentrated aerosol. It was found that the two nebulizers delivered a roughly equivalent amount of protein to an animal when the devices were operated until the initial charge of 5 mL was exhausted and aerosol generation became erratic (10 or 15 minutes for the Acorn II depending on the operating air flow rate, and 20 minutes for the Ultravent).

TABLE 1

AEROSOL CONCENTRATION AND INHALATION DOSE ESTIMATES FOR TWO JET NEBULIZERS USING A 20 mg/ml ALBUMIN SOLUTION

| Nebulizer (airflow) | Aerosol Conc. ($\mu$g/L $\pm$ SEM) | MMAD ($\mu$m)* GSD | Period (min.) | Delivered Dose ($\mu$g $\pm$ SEM) |
|---|---|---|---|---|
| Ultravent | outlet 126 $\pm$ 13 | 0.93 | 20 | 76 $\pm$ 8 |
| (10 L/min) | nose 141 $\pm$ 17 | 3.6 | 20 | 85 $\pm$ 10 |
| Acorn II | outlet 239 $\pm$ 48 | 2.8 | 15 | 107 $\pm$ 29 |
| (8 L/min) | nose 297 $\pm$ 2 | 2.9 | 15 | 133 $\pm$ 3 |
| (10 L/min) | outlet 362 | — | 10 | 109 |

*MMAD = Mass median aerodynamic diameter;
GSD = Geometric standard deviation;
SEM = Standard error of the mean of three determinations.

An estimate of the amount of G-CSF delivered via aerosol to a hamster during an inhalation exposure from a nebulizer was determined from the following expression:

$$D = \eta V C \Delta t$$

where D is the inhalation dose, $\eta$ is the fractional deposition, V is the ventilation rate, C is the aerosol concentration, and $\Delta t$ is the period of administration. By using the measured aerosol concentration (C) and operating period ($\Delta t$) of the nebulizer, along with the resting ventilation rate (V) for a mature hamster of 30 mL/min and a fractional deposition ($\eta$) of 0.5, it was determined that G-CSF concentrations of between 5 mg/mL and 10 mg/mL of nebulizer solution would result in an inhalation dose of 100 $\mu$g/kg (e.g., 10 $\mu$g for a 100 g hamster). This was the dose estimated to produce a maximal neutrophil response via pulmonary delivery.

Aerosol Administration of G-CSF to Hamsters

The solutions used to conduct aerosol exposures were prepared by reconstituting lyophilized rhG-CSF in sterile distilled water containing 1 mg/mL of the nonionic surfactant polyoxyethylenesorbitan monooleate. The solutions used in the nebulizer to generate the exposure aerosols were prepared with G-CSF in concentrations ranging from 1 to 15 mg/mL.

Groups of ten hamsters (mature, male Golden Syrian) were exposed to aerosols containing rhG-CSF. The hamsters were placed in restraining tubes and allowed to acclimate for approximately 5 minutes. The tubes were then inserted into the exposure chamber and the aerosol exposure was initiated. Following exposure, the hamsters were returned to their cages and given free access to food and water. Blood samples were taken 24 hours after exposure, and the blood neutrophil concentration was determined by the same procedure used to evaluate the blood samples following subcutaneous injection.

The aerosol concentration and particle size distribution were measured during each exposure. The G-CSF dose was varied from one exposure to another by using different concentrations of G-CSF in the nebulizer solution.

Figure 2:
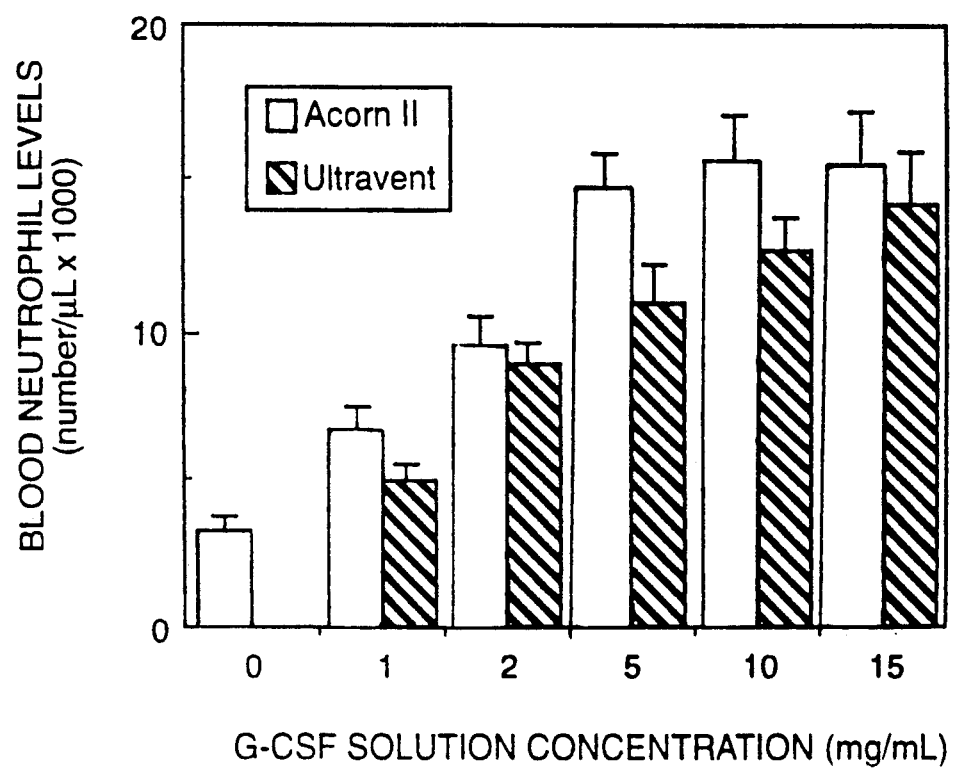
FIG. 2 is a bar graph of the blood neutrophil levels in hamsters following exposure to aerosols generated from either an Acorn II nebulizer or an Ultravent nebulizer, using different concentrations of rhG-CSF in aqueous solution.

Hamsters exposed to aerosols containing G-CSF were found to have elevated neutrophil concentrations when compared to untreated animals and animals exposed to an aerosol containing only water and surfactant (polyoxyethylene sorbitum monooleate). FIG. 2 shows the increase in neutrophil counts observed in animals exposed to aerosols generated from rhG-CSF nebulizer solutions ranging in concentration as described. As can be seen, the circulating neutrophil levels obtained from G-CSF aerosol exposure, even with as low a concentration as 1 mg/mL of G-CSF (using the Ultravent nebulizer), were significantly higher ($p<0.05$) than the group exposed to an aerosol without G-CSF. The statistical significance of the increase in neutrophil levels over the control was $p<0.001$ for all the other groups. The increase in blood neutrophil levels correlated with increasing G-CSF concentration in the nebulizer solution up to a concentration of 5 mg/mL. A maximum response of 15,000 neutrophils per $\mu$L of blood was observed with the more concentrated G-CSF nebulizer solutions, similar to the maximum obtained with subcutaneous injection of doses greater than 50 $\mu$g/kg. There was virtually no difference in neutrophil response obtained with the two nebulizers using lower G-CSF solution concentrations, e.g., below 5 mg/mL. For G-CSF solution concentrations greater than 5 mg/mL, the Acorn II nebulizer produced a greater increase in neutrophil response than the Ultravent.

An inhalation exposure to an aerosol generated from a 5 mg/mL G-CSF solution that did not contain surfactant produced a neutrophil response ($9,910\pm960$ neutrophils/$\mu$L) in hamsters not significantly different from that obtained with either a 50 $\mu$g/kg subcutaneous injection containing surfactant ($10,935\pm1,390$ neutophils/$\mu$L) or a 50 $\mu$g/kg subcutaneous injection prepared from the solution lacking surfactant ($10,270\pm430$ neutrophils/$\mu$L). These values are reported as the mean and standard error of ten animals for the aerosol tests and five animals for the injections. From this experiment, it was concluded that the surfactant was not a necessary component of the aqueous aerosol formulation for G-CSF.

Fractional Deposition of G-CSF Aerosol in Hamster Lungs

The dose delivered to the animal during an exposure was estimated in order to ascertain whether therapeutic amounts of G-CSF can be effectively and economically delivered via the lung. The delivered or deposited dose is the product of the amount of drug the animal inhales and the efficiency (fractional deposition) with which the aerosol particles deposit in the lung. The latter was determined by measurement of the amount of G-CSF recovered from the hamster lungs following aerosol exposure.

G-CSF deposited in the lungs was measured in two groups of four animals exposed to aerosols generated with the Acorn II nebulizer. Immediately following aerosol exposure, the whole lungs of four hamsters were removed, placed into glass tissue grinders containing 3 mL of cold physiological buffered saline, and homogenized. The homogenate was centrifuged twice, and the final supernatent was transferred to a clean tube and assayed for G-CSF using radioimmunoassay (Amgen Inc., Thousand Oaks, Calif.). In control experiments using this procedure, it was determined that 75% of the G-CSF could be recovered from samples of lung homogenate spiked with a known amount of G-CSF. All measurements of G-CSF in the lungs following aerosol exposure were corrected for this fractional recovery of G-CSF from lung tissue.

An average of $3.1\pm0.3$ $\mu$g of G-CSF was deposited in the lung in the group of animals exposed for 11 minutes to an aerosol generated from a 5 mg/mL solution of the protein. An average of $20.0\pm4.0$ $\mu$g of G-CSF was deposited in the animal group exposed for 11 minutes to an aerosol generated from a 20 mg/mL solution. Based on the concentration of G-CSF in the aerosol measured during the exposure and the resting ventilation rate (30 mL/min), the animals in the 5-mg/mL group inhaled 22 $\mu$g of G-CSF (68 $\mu$g/L$\times$0.030 L/min$\times$11 min), and the 20-mg/mL group inhaled 69 $\mu$g of G-CSF (208 $\mu$g/L$\times$0.030 L/min$\times$11 min) over an exposure period. Using the amounts of G-CSF inhaled and the amounts recovered from the lung, the deposition efficiency (fractional deposition$\times$100) in the lung was estimated to be 14% for the 5-mg/mL group and 29% for the 20-mg/mL group.

The fractional deposition determined from the G-CSF measured in the lungs following aerosol exposure was then used to estimate the G-CSF dose administered by aerosol, in order to relate the increase in the neutrophil concentration to the aerosol dose.

Table 2 contains the inhaled and deposited doses estimated for the aerosol exposures using various concentrations of G-CSF in the nebulizer solution. The G-CSF aerosol concentration was measured gravimetrically from a filter sample collected during the exposure and the weight was corrected for the proportion of surfactant (1 mg/mL) to G-CSF in solution. The inhaled dose was calculated from the aerosol concentration, the resting ventilation rate (30 mL/min), and the exposure period (11 minutes for the Acorn II and 20 minutes for the Ultravent). The deposited dose was calculated from the inhaled dose and the measured fractional deposition (0.29).

TABLE 2

THE ESTIMATES OF G-CSF DELIVERED TO THE LUNG DURING AEROSOL EXPOSURES

| Solution Conc. (mg/ml) | [C]* ($\mu$g/L) | Inhaled Dose ($\mu$g) | Deposited Dose ($\mu$g) | Mean Body Weight (g) | Estim. Dose/ Body Wt ($\mu$g/kg) |
|---|---|---|---|---|---|
| Acorn II Nebulizer ||||||
| 1 | 8 | 2.6 | 0.75 | 66.7 | 11 |
| 2 | 10 | 3.3 | 0.96 | 76.3 | 13 |
| 5 | 73 | 24 | 7.0 | 92.2 | 76 |
| 10 | 109 | 36 | 10 | 83.3 | 125 |
| 15 | 188 | 62 | 18 | 86.1 | 209 |
| Ultravent Nebulizer ||||||
| 1 | 2.5 | 1.5 | 0.44 | 63.3 | 6.9 |
| 2 | 2.7 | 1.6 | 0.46 | 77.1 | 6.1 |
| 5 | 33 | 20 | 5.7 | 91.2 | 63 |
| 10 | 41 | 25 | 7.1 | 84.8 | 84 |
| 15 | 38 | 23 | 6.6 | 81.5 | 81 |

*The filter weight was corrected for 1 mg/ml surfactant to obtain the G-CSF concentration in the aerosol.

Figure 3:
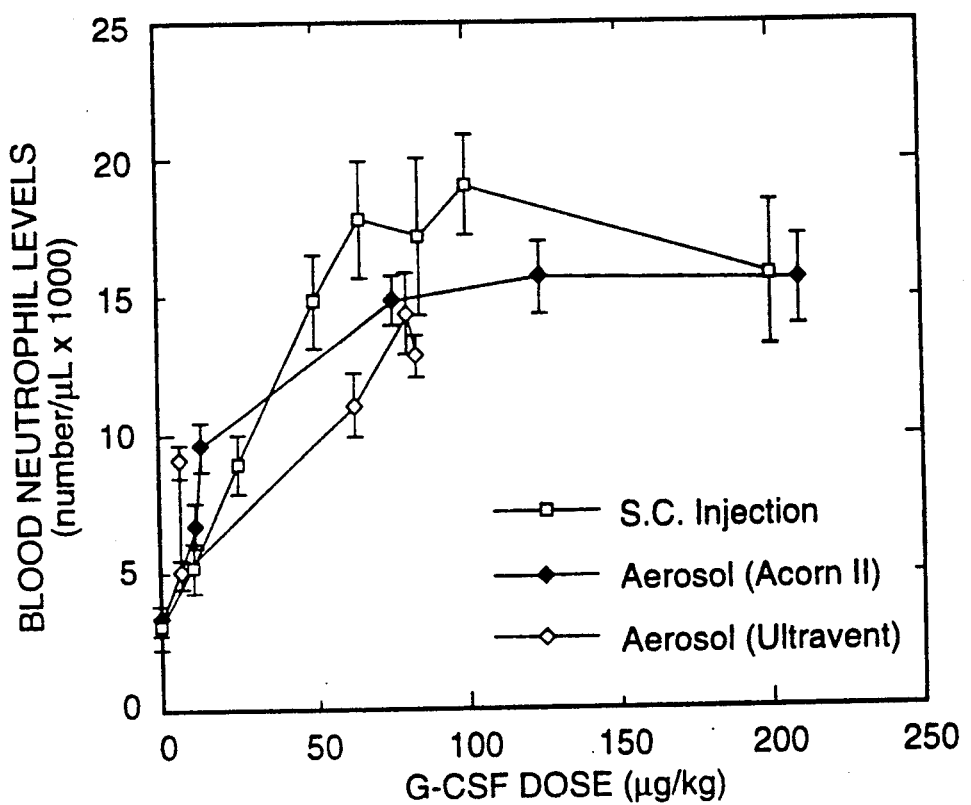
FIG. 3 depicts a comparison of blood neutrophil levels resulting from subcutaneous and aerosol administration of rhG-CSF.

FIG. 3 shows the neutrophil response following subcutaneous injection and the aerosol administration of G-CSF for the dose levels calculated above. Comparing the neutrophil response obtained with an aerosol to that obtained by subcutaneous injection shows that, for the therapeutically important dose range of 1 to 100 $\mu$g/kg, the deposited dose is approximately equivalent to an injection.

While this invention has been specifically illustrated with regard to the use of aerosolized solutions and nebulizers, it is to be understood that any conventional means suitable for pulmonary delivery of a biological material may be employed to administer G-CSF in accordance with this invention. Indeed, there may be instances where a metered dose inhaler, or powder inhaler, or other device is preferable or best suits particular requirements. The foregoing description provides guidance as to the use of some of those devices. The application of still others is within the abilities of the skilled practitioner. Thus, this invention should not be viewed as being limited to practice by application of only the particular embodiments described.

What is claimed is:

1. A method for the pulmonary administration of G-CSF to a mammal, comprising directing a neutrophil stimulating amount of G-CSF into the oral cavity of the mammal while the mammal is inhaling for those is need thereof.

2. A method according to claim 1, wherein G-CSF is administered in the form of a pharmaceutical composition comprising G-CSF in a pharmaceutically acceptable carrier.

3. A method according to claim 2, wherein the composition is in the form of a solution in an aqueous medium or a suspension in a non-aqueous medium.

4. A method according to claim 2, wherein the composition is in the form of a dry powder.

5. A method according to claim 4, wherein G-CSF has a particle size of less than 10 microns.

6. A method according to claim 4, wherein the G-CSF has a particle size between 1 and 5 microns.

7. A method according to claim 2, wherein the G-CSF is human G-CSF.

8. A method according to claim 7, wherein the human G-CSF is recombinant human G-CSF.

9. A method according to claim 8, wherein the recombinant human G-CSF is the product of expression in a transformed eucaryotic or procaryotic host cell.

10. A method according to claim 9, wherein the host cell is procaryotic.

11. A method according to claim 10, wherein the host cell is *E. coli.*

12. A method according to claim 1, wherein G-CSF is delivered from a mechanical device suitable for pulmonary administration and capable of depositing G-CSF in the lungs of the mammal.

13. A method according to claim 12, wherein the device is a nebulizer, metered dose inhaler or powder inhaler.

14. A method according to claim 13, wherein the device is a jet nebulizer.

15. A method according to claim 13, wherein the device is an ultrasonic nebulizer.

16. A method according to claim 1 wherein the mammal is a human.

17. A method according to claim 16, wherein the administration results in blood neutrophil levels in excess of 1000 neutrophils per $\mu$L of blood.

18. A method according to claim 16, wherein the administration results in blood neutrophil levels of about 5000 to 6000 neutrophils per $\mu$L of blood.

19. The method of claim 1 which is used to treat neutropenia.

20. The method of claim 1 which is used to treat infection.

21. The method of claim 1 which is used to prevent infection.

* * * * *